US009095469B2

(12) United States Patent
Nayak et al.

(10) Patent No.: US 9,095,469 B2
(45) Date of Patent: Aug. 4, 2015

(54) METHOD AND APPARATUS TO REMOVE CAST FROM AN INDIVIDUAL

(71) Applicants: Suresh Nayak, Cincinnati, OH (US);
Ronald R Watson, Scottsdale, AZ (US)

(72) Inventors: Suresh Nayak, Cincinnati, OH (US);
Ronald R Watson, Scottsdale, AZ (US)

( * ) Notice: Subject to any disclaimer, the term of this patent is extended or adjusted under 35 U.S.C. 154(b) by 57 days.

(21) Appl. No.: 13/998,026

(22) Filed: Sep. 24, 2013

(65) Prior Publication Data

US 2014/0039509 A1 Feb. 6, 2014

Related U.S. Application Data

(63) Continuation-in-part of application No. 13/373,890, filed on Dec. 5, 2011, now Pat. No. 8,539,866, which is a continuation-in-part of application No. 12/799,711, filed on Apr. 30, 2010, now Pat. No. 8,069,760, which is a continuation-in-part of application No. 12/315,212, filed on Dec. 1, 2008, now Pat. No. 8,042,439.

(51) Int. Cl.
| B27B 9/04 | (2006.01) |
| A61F 15/02 | (2006.01) |
| B23D 47/02 | (2006.01) |
| B23D 51/02 | (2006.01) |

(52) U.S. Cl.
CPC .............. *A61F 15/02* (2013.01); *B23D 47/02* (2013.01); *B23D 51/025* (2013.01); *B27B 9/04* (2013.01)

(58) Field of Classification Search
CPC .......... B26D 7/0006; B27B 9/04; B23D 1/00; B23D 1/006; B23D 1/08; A61F 5/04; A61F 5/01; A61F 5/013; A61F 15/02; A61F 2005/0144
USPC ............... 83/13, 613, 636, 821; 30/370, 90.1, 30/90.6, 90.4, 289, 290, 294, 297, 314, 30/317; 606/138, 105, 105.5; 602/8–10, 5
See application file for complete search history.

(56) References Cited

U.S. PATENT DOCUMENTS

| 2,187,175 | A | * | 1/1940 | Prosperi | 602/9 |
| 2,206,339 | A | * | 7/1940 | Ulman, Jr. | 602/9 |
| 2,230,781 | A | * | 2/1941 | Longfellow | 602/9 |
| 2,490,878 | A | * | 12/1949 | Marsh | 30/276 |
| 2,519,520 | A | * | 8/1950 | Waxlax | 602/9 |
| 2,523,837 | A | * | 9/1950 | Luger | 602/9 |
| 2,837,088 | A | * | 6/1958 | Moses | 602/14 |
| 3,867,931 | A | * | 2/1975 | Babka | 602/9 |
| 3,985,129 | A | * | 10/1976 | Huene | 602/9 |
| 4,129,127 | A | * | 12/1978 | Ellison | 602/12 |
| 4,625,405 | A | * | 12/1986 | Hudnutt et al. | 30/370 |
| 5,435,066 | A | * | 7/1995 | Bare et al. | 30/388 |
| 5,944,675 | A | * | 8/1999 | Bequet-Sharber et al. | 602/9 |

* cited by examiner

*Primary Examiner* — Phong Nguyen
(74) *Attorney, Agent, or Firm* — Tod R. Nissle, P.C.

(57) ABSTRACT

A method for installing a fiberglass cast on and removing the cast from an individual includes an open ended pliable thin-walled polymer guide track and cutting tool designed to track along said guide track to cut the cast and to prevent, while a cast is being removed, injury to the individual.

1 Claim, 15 Drawing Sheets

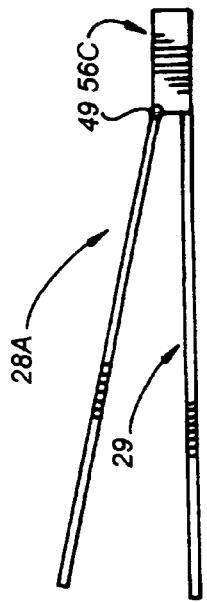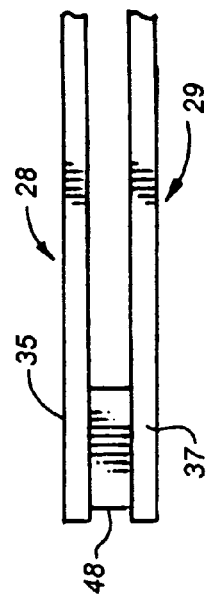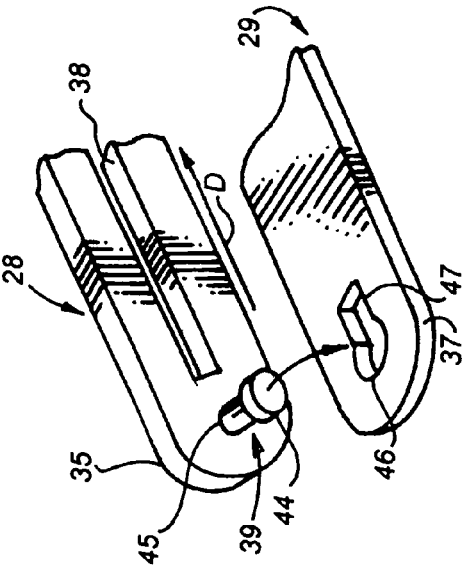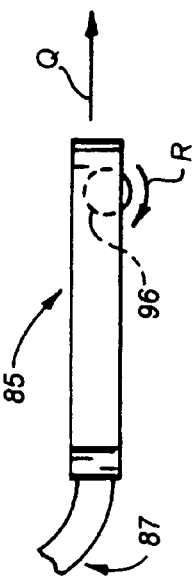

METHOD AND APPARATUS TO REMOVE CAST FROM AN INDIVIDUAL

This is a continuation-in-part of and claims priority based upon patent application Ser. No. 13/373,890, filed Dec. 5, 2011, which application is a continuation-in-part of and claims priority based upon patent application Ser. No. 12/799,711 filed Apr. 10, 2010, which application is a continuation in-part of and claims priority based upon patent application Ser. No. 12/315,212, filed Dec. 1, 2008.

This invention relates to casts that are temporarily placed on individual's skeletal or muscular structure. One common use of a cast is to support the leg, arm, or other part of the body.

More particularly, the invention pertains to a method and apparatus for removing such casts.

First Trend

A first trend in connection with the removal of a cast comprises placing an elongate tubular guide or channel on a portion of the body of an individual prior to applying the cast and permitting the cast to solidify. The cast, when applied, covers the tubular guide. When the time comes to remove the cast an elongate cutting wire is fed through the tubular guide. The cutting wire is moved back and forth to outwardly cut through the cast, or is otherwise forced outwardly through the cast to cut the cast. One common cutting wire is identified by the name Giggli saw.

Second Trend

A second trend in connection with the removal of a cast comprises placing an elongate tubular guide or channel on a portion of the body of an individual prior to applying the cast and permitting the cast to solidify. The cast, when applied, covers the tubular guide. When the time comes to remove the cast a scissors tool is utilized to cut through the cast. The tubular guide helps to direct the scissors.

Third Trend

A third trend in connection with the removal of a cast comprises utilizing a shield comprising an elongate relatively flat strip of material. The shield is placed on a portion of the body of an individual prior to applying the cast and permitting the cast to solidify. The cast, when applied, covers the flat strip of material. When the time comes to remove the cast with a cutting tool, the flat strip of material functions to shield the individual from a cutting tool.

Fourth Trend

A fourth trend in connection with the removal of a cast comprises utilizing a tool with a rigid foot that a user slides along a shield strip or guide channel. The tool also includes a rotary cutting tool that is situated above the fixed foot and cuts the cast. The tool utilizes a circular, flat, thin blade with teeth situated around the circular peripheral edge of the blade.

Fifth Trend

A fifth trend in connection with the removal of a cast comprises utilizing a Stryker saw or similar tool to remove a cast. A Stryker saw includes a housing and a saw blade rotatably mounted on the housing. The saw blade is a panel-shaped, relatively thin, flat, circular blade with cutting or abrading material formed on the sides of the blade near the circular outer peripheral edge of the blade. The outer peripheral edge of the blade does not include abrading or cutting material; this to minimize the likelihood that the outer edge of the blade will cut the skin of an individual. The rapid rotation of the blade can, however, cause the outer peripheral edge to burn or cut the skin of an individual on contact. A user grasps the housing and uses the saw blade to cut through a cast while endeavoring not to contact and injure the skin of the individual. The Stryker saw can be, but often is not, utilized in connection with a protective strip or with a guide. The user simply does his or her best to guide and control the saw and to not inadvertently burn or cut the skin of an individual. Such inadvertent injury does, however, occur on a fairly regular basis. Further, the noise associated with use of the saw often effectively functions to terrify children who are having a cast removed. Such fear on the part of a child and the child's parent is magnified when a user inadvertently contacts and burns or cuts the skin of the child with the saw blade.

The Stryker saw is currently by far the presently preferred, and usually the only, method of removing a cast. The methods and tools set forth above with respect to the third trend are currently sometimes used on a limited basis in the market. However, the methods and tools set forth above in the first through the fourth trends otherwise are basically largely, if not entirely, obsolete, are currently ignored, and in the real world exist only in the print and paper comprising earlier issued patents, magazine articles, and other documents.

The Stryker saw has evidently been the preferred method of removing a cast for at least the last twenty (20) years; any perceived motivation to provide an alternate method or removing a cast has not provided sufficient impetus to displace use of the Stryker saw, or to reinstate the obsolete methodology set forth in prior issued patents or other documents.

Nonetheless, it is a principal object of the invention is to develop an improved method and apparatus to remove a cast, in particular a fiberglass cast, from an individual. A fiberglass cast is significantly more difficult to cut than was the old fashioned plaster cast.

This and other, further and more specific objects and advantages of the invention will be apparent to those skilled in the art from the following detailed description thereof, taken in conjunction with the drawings, in which:

FIG. 20 is a partial perspective view of the guide assembly of FIGS. 18 and 19 illustrating an alternate construction thereof;

FIG. 21 is a side view of the guide foot of FIG. 16 illustrating an alternate construction thereof to facilitate rolling contact by the guide foot;

FIG. 22 is a side view illustrating an alternate construction of the guide assembly of FIGS. 18 and 19;

FIG. 23 is a partial side view of the guide assembly of FIGS. 18 and 19 illustrating an alternate construction thereof; and, FIG. 24 is an exploded perspective view further illustrating a portion of the guide assembly of FIGS. 18 and 19.

Figure 1:
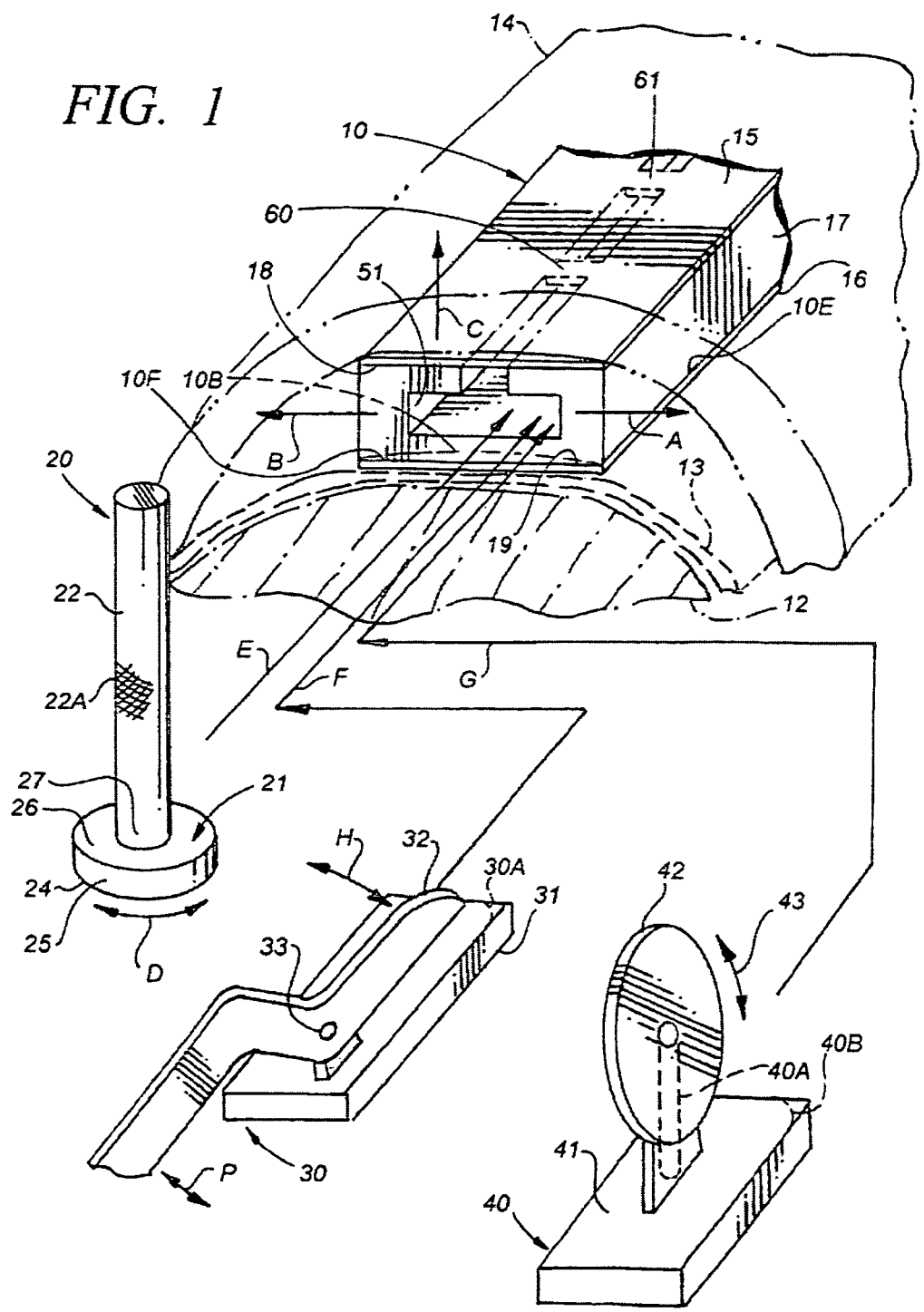
FIG. 1 is an exploded perspective view illustrating apparatus constructed in accordance with the principles of the invention and the mode of operation thereof.

Briefly, in accordance with the invention we provide an improved method of installing a fiberglass cast on and removing the cast from an individual. The method comprises the step of providing a track (10) with a top; a bottom; a length (L); an elongate primary guide opening (11) extending the length of the track, the opening having a width (W) and a selected shape and dimension; and, an elongate secondary guide opening (18A) extending from the primary opening upwardly to the top of the track, and having a width less than the primary opening. The method also comprises the step of providing a rotatable bit (20) including a rotatable shaft (22) and a tracking foot (21). The shaft has an outer surface shaped and dimensioned to cut through a fiberglass cast; a width less than the width of the secondary guide opening; a distal end (27); and, is shaped and dimensioned to move along the secondary opening. The tracking foot is foot (21) is attached to the distal end of the shaft; has an outer surface (25); has a width greater than the width of the shaft (22) and less than the width of the primary opening, is free of cutting surfaces, and is shaped and dimensioned to generally conform to the shape and dimension of the primary guide opening to minimize lateral movement of the foot in the primary guide opening and to permit the foot to move freely along the primary opening. The method also includes the steps of placing the track (10) on an individual; applying at a first selected time a fiberglass cast on the individual, the cast covering substantially all of the track (10); and, at a second selected time subsequent to the first time, rotating the bit and moving the foot along the primary opening and the shaft along the secondary opening such that the shaft cuts through the fiberglass cast.

In another embodiment of the invention, provided is a method of installing a fiberglass cast on and cutting the cast for removal from an individual. The method includes the steps of providing a length of a pliable hollow thin-walled guide tube (110) with a top, a bottom, a length, and open first and second ends; providing an elongate support tool (55) shaped and dimensioned to slide into and extend along the tube (110); and, providing a cutting tool. The cutting tool includes a housing; a motor unit mounted in the housing; a rotatable shaft with a proximate end mounted on the motor unit, and with a distal end having an outer cutting surface shaped and dimensioned to cut through a fiberglass cast, the shaft being rotated by the motor; and, a guide tool mounted on the housing and including a tracking foot positioned beneath the cutting surface and shaped and dimensioned to fit in and slide along the pliable guide tube. The method also includes the steps of sliding said support tool in said pliable guide tube; placing the guide tube and support tube on an individual; applying at least first layer of fiberglass along and over a portion of the guide tube excluding the first end of the guide tube; wrapping the first end of said guide tube over said first layer of fiberglass to form a loop extending around said first layer of fiberglass; applying at least a second layer of fiberglass along and over the portion of the guide tube and the first end of the guide tube to affix the first end of the guide tube between the first and second layers of fiberglass; sliding the support tool out of the guide tube; and, allowing the first and second layers of fiberglass to harden; and, at a subsequent time, cutting the loop, and manipulating the tool to insert the guide foot in the guide tube and slide the guide foot along the tube while cutting through the fiberglass layers with the outer cutting surface.

In a further embodiment of the invention, provided is an improved method of installing a fiberglass cast on and cutting the cast for removal from an individual. The improved method comprises the steps of providing a length of a pliable hollow thin-walled guide tube (110) with a top, a bottom, a length, and open first and second ends; providing an elongate support tool (55) shaped and dimensioned to slide into and extend along the tube (110); providing a cutting tool including a housing (77), a motor unit mounted in the housing, a blade (80) oscillated by the motor unit; a guide (70) including an upper leg (71) with a guide slot (72) formed therealong, and a lower leg (75) spaced apart from the upper leg, the lower leg (75) shaped and dimensioned to fit in and slide along the pliable guide tube; sliding the support tool in the pliable guide tube; placing the guide tube and support tube on an individual; applying at least first layer of fiberglass over a portion of the guide tube; applying at least a second layer of fiberglass along and over the first layer of fiberglass; sliding the support tool out of the guide tube; allowing the first and second layers of fiberglass to harden; and, at a subsequent time, inserting the lower leg of the guide (70) in the tube with the upper leg of the guide extending over the cast, and, using the blade (80) of the cutting tool to track along the guide slot (72) and cut through the first and second layers of fiberglass.

In still another embodiment of the invention, provided is an improved method of installing a fiberglass cast on and cutting the cast for removal from an individual. The improved method includes the steps of providing a length of a pliable hollow thin-walled guide tube (110) with a top, a bottom, a length, and open first and second ends; of providing an elongate support tool (55) shaped and dimensioned to slide into and extend along the tube (110); of providing a tool including a manually displaceable housing (77), a motive power unit, a cutting tool mounted in the housing and operated with said motive power unit; of providing a guide (70) including an upper leg (71) with a guide slot (72) formed therealong, and a lower leg (75) spaced apart from the upper leg, the lower leg (75) shaped and dimensioned to fit in and slide along the pliable guide tube; of sliding the support tool in the pliable guide tube; of placing the guide tube and support tube on an individual; of applying at least a first layer of fiberglass over a portion of the guide tube; of applying at least a second layer of fiberglass along and over the first layer of fiberglass; of sliding the support tool out of the guide tube; of allowing the first and second layers of fiberglass to harden; and, of, at a subsequent time, inserting the lower leg of the guide (70) in the tube with the upper leg of said guide extending over the cast, and manually pushing the housing along the upper leg of the guide such that the cutting tool extends through and tracks along the guide slot (72) and cuts through the first and second layers of fiberglass.

Turning now to the drawings, which depict the presently preferred embodiments of the invention for the purpose of illustrating the practice thereof and not by way of limitation of the scope of the invention and in which like reference characters refer to corresponding elements throughout the several views, FIG. 1 illustrates a track generally indicated by reference character 10. Track 10 preferably is, as will be described, somewhat pliable and is not rigid. Such pliability permits the track 10 to conform to the body of an individual. Track 10 includes top 18, bottom 19, and side 17. Primary opening 11 extends along the length (L) (FIG. 3) of track 10. Primary opening 11 includes and is circumscribed by vertically oriented sides 51 and 52, horizontally oriented bottom 50, and ceiling 53. As can be seen, primary opening 11 currently preferably has a rectangular cross section. The shape and dimension of opening 11 can, however, vary as desired and have, by way of example, a triangular, trapezoidal, or spherical cross section. If desired, the bottom of track 10 can, instead of being flat, be provided with a concave contour 10B (FIGS. 1 and 3) to enable track 10 to better contour to an arm or other portion of an individual's body. Similarly, if desired, the lower parallel outer edges 10E and 10F of track 10 can, instead of comprising straight edges, be rounded or provided with a radius as indicated by dashed line 10C and 10D in FIG. 2. The use of rounded edges 10C and 10D reduces the likelihood that edges 10E and 10F will generate uncomfortable pressure points in the tissue of an individual.

Secondary opening 18A also extends along the length (L) of track 10, and, extends upwardly from opening 11 to the top 18 of track 10. The width of opening 18A is less than the width W of the primary opening 11 and is greater than the width S of shaft 22 of bit 20 (FIG. 1).

Figure 2:
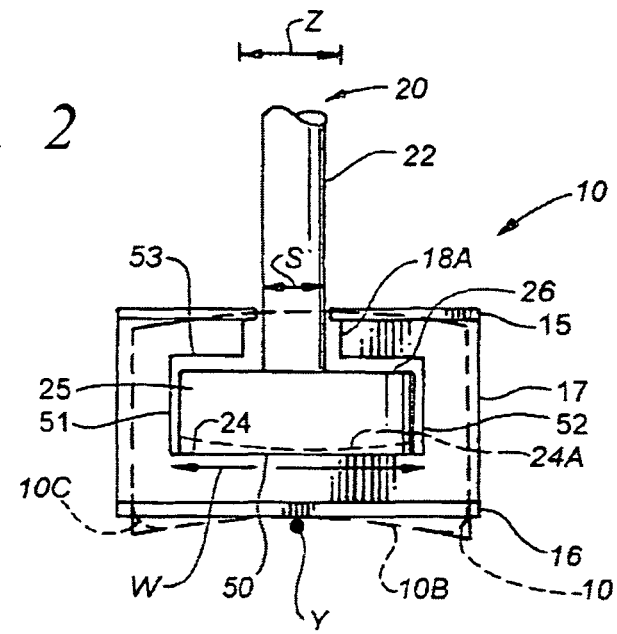
FIG. 2 is a front view further illustrating the mode of operation of one of the embodiments of the invention.

As is illustrated in FIGS. 1 and 2, an adhesive strip 16 can, if desired, be applied to track 10 and extend along the bottom 19 of track 10. Strip 16 can, if desired, be covered with a protective strip of paper or other material. The protective strip is peeled off strip 16 prior to emplacing strip 10 on an individual when a cast is being applied to the individual.

A protective strip of material 15 (FIG. 1) can, if desired, be applied to the top 18 of track 10 to cover secondary opening 18. Strip 15 is preferred because it prevents fiberglass or other material from entering openings 18A and 11 when a cast is being formed over track 10. The strip 15 is preferably formed of a thin sheet of paper, polymer, or some other material that can readily be cut by bit 20 when foot 21 moves along the length of opening 11. In an alternate embodiment of the invention, ribs or bridge structures 60, 61 extend across strip 15 at selected spaced apart locations along the length of opening 18. Ribs 60, 61 can be utilized in place of or in conjunction with strip 15.

Figure 3:
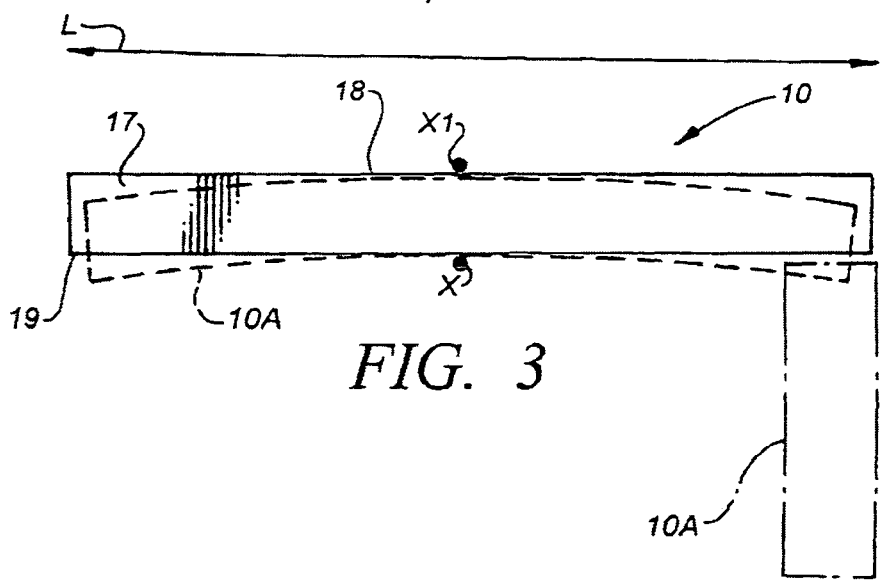
FIG. 3 is a side elevation view illustrating the mode of operation of a track utilized in the practice of the invention.

Track 10 preferably is somewhat pliable along its length such that track 10 will bend downwardly longitudinally in the manner indicated by dashed lines 10A about an axis X (of upwardly about on axis X1) that in FIG. 3 is perpendicular to the plane of the sheet of paper of the drawing. This permits track 10 to conform to the body of an individual. On the other hand, it is preferred to limit the ability of track 10 to bend transversely about an axis Y that in FIG. 3 is perpendicular to the plane of the sheet of paper of the drawing. In other words, track 10 is transversely substantially rigid. Transverse rigidity is important because it significantly reduces the likelihood that track 10 will transversely bend and then bind foot 21 as it moves along track 10.

Bit 20 includes cutting shaft 22 and foot 21 fixedly attached to the distal end 27 of shaft 22. The outer surface 22A of shaft 22 is serrated or otherwise shaped and dimensioned and configured to cut through strip 15 and ribs 60 and 61 when bit 20 rotates about the longitudinal axis of bit 20. Proximate, or upper, end of shaft 22 is engaged by a drill chuck (not shown) or other apparatus that rotates bit 20. Foot 21 includes upper surface 26, bottom surface 24, and peripheral cylindrically shaped outer surface 25. Bottom surface 24 can, as indicated by dashed line 24A in FIG. 2, have a convex shape to facilitate movement of foot 21 along primary opening 11. Foot 21 is shaped and dimensioned generally to fit in, conform to, and move along primary opening 11. In this manner, when foot 21 is slid or otherwise moved along the length of opening 11, opening 11 restricts lateral movement of foot 21 in the directions of arrows A and B and restricts vertical movement of foot 21 upwardly in the direction of arrow C (FIG. 1). Primary opening in essence functions to "capture" foot while permitting foot 21 to be freely moved along the length of opening 11 while bit 20 is rotating. The rounded cylindrical outer surface 25 of bit 20 provides a minimal contact area in the event foot 21 bears against a side 51, 52. Bottom surface 24 readily rotates over bottom 50 of opening 11. Bottom surface 24 of foot 21 preferably, but not necessarily, has a convex shape to minimize the area of surface 24 that is contact with bottom 50 at any given time.

Rectangular foot 40 (FIG. 1) is, in a manner similar to foot 21, shaped and dimensioned to fit in and freely slide along opening 11. A saw blade 42 is mounted on the top 41 of foot 40 to rotate in a selected one of the directions indicated by arrows 43. A motor or other motive power (not shown) is provided to turn blade 42 such that it cuts through a fiberglass cast while foot 40 travels along the length of opening 11.

Rectangular foot 30 (FIG. 1) is, in a manner similar to feet 21 and 40, shaped and dimensioned to fit in and freely slide along opening 11. A scissor jaw 32 is pivotally 33 mounted on foot 30 and pivotally reciprocated in the manner indicated by arrows H to cut through a fiberglass cast while foot 30 travel along the length of opening 11.

In use, a strip of soft cast padding/stockingette material is wrapped 13 (FIG. 1) around an arm, leg, or other body area on which a cast is to be mounted. The protective paper or polymer strip (not shown) covering adhesive layer 16 is removed, and track 10 is placed on the arm generally parallel to the longitudinal axis of the arm. Adhesive layer 16 secures track 10 to the layer of cotton lining material, (or to a layer(s) of another material or to the skin if such a layer is not utilized. A fiberglass cast 14 is then applied around the arm and is allowed to harden. The fiberglass cast 14 covers substantially the entire length of track 10 except, however, the ends of track 10 are left exposed, or accessible, to facilitate the use of bit 20. At some subsequent time, the cast needs to be removed. At that time, bit 20 is rotated, and foot 21 is moved into one end of primary opening 11 in the manner illustrated in FIG. 2 and is moved along the entire length of opening 11 to cut the fiberglass cast. When foot 21 moves into opening 11, shaft 22 extends upwardly through secondary opening 18A and simultaneously cuts through strip 15 and the portion of cast 14 positioned directly above secondary opening 18A. A portion of rotating shaft 22 moves along secondary opening 18A (FIG. 2) simultaneously with the movement of foot 21 along primary opening 11.

Figure 4:
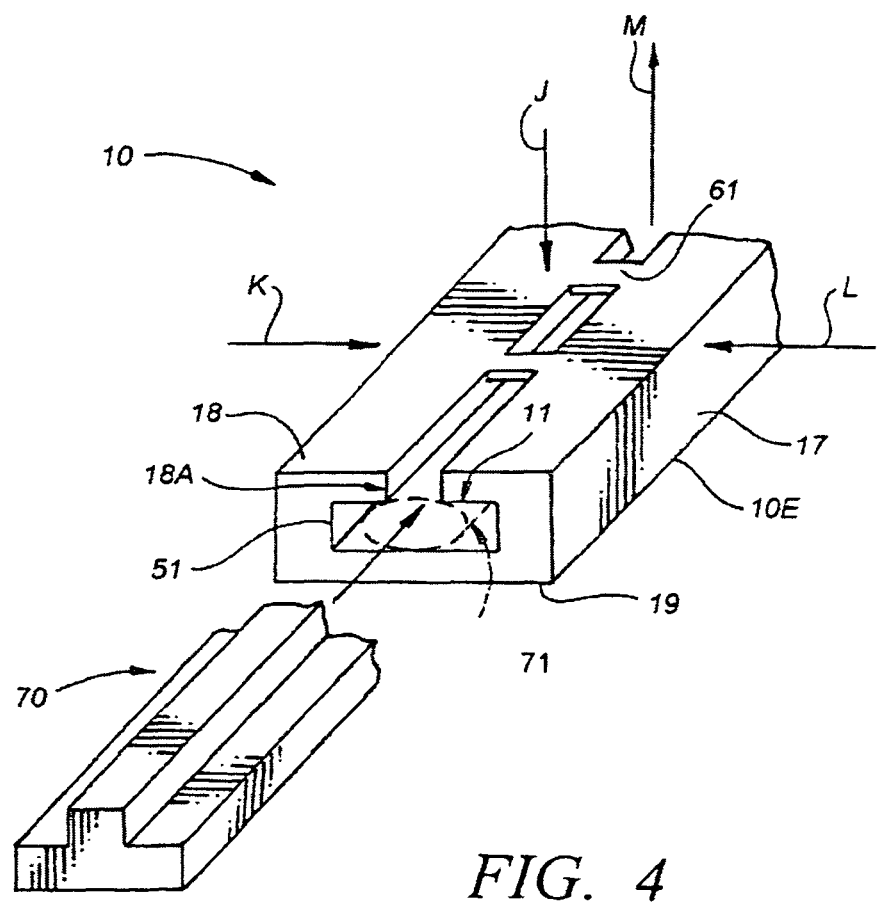
FIG. 4 is an exploded perspective view illustrating apparatus constructed in accordance with the principles of the invention and illustrating a removable insert utilized to strengthen the apparatus during the application of a cast to an individual.

In one preferred embodiment of the invention, when bit 20 is rotated and foot 21 is moved along opening 11 to cut through cast 14, bit 20 is pulled upwardly in the direction of arrow M (FIG. 4). The magnitude of the force generated in the direction of arrow M can vary as desired, but ordinarily is relatively small and, in contrast to a Stryker saw, is sufficient to insure that track 10 is not downwardly pressed against the body of the individual while bit 20 cuts through cast 14. If the magnitude of force M is too great, the friction forces generated when rotating foot 21 bears against ceiling 53 can unnecessarily impede the ready movement of foot 21 along opening 11.

FIG. 1 illustrates only a single track 10 on the arm of an individual. As would be appreciated by those of skill in the art, cast 14 ordinarily needs to cut along two opposing sides to be removed. Accordingly, a second track (not visible in FIG. 1) is placed on layer 13 on the opposite side of the arm at the same time track 10 is placed on layer 13. When cast 14 is applied, it covers both tracks. In other words, the procedure for installing the second track is equivalent to that for installing track 10. When the time comes to remove a fiberglass cast 14, rotating bit 20 is moved along track 10 to make one cut through cast 14, and is then moved along the second track to make a second cut through cast 14. The two cuts function to halve the cast to permit ready removal of the cast from the individual's arm.

A length of track 10 can be wound and stored on a roll such that a desired length of track 10 can be pulled off the roll and cut from the roll, much like rope is stored on a large roll and desired lengths of rope are measured and cut from the rope remaining on the roll.

In some instances, a cast 14 made from fiberglass or an equivalent material is applied to portions of an individual's body that are at an angle to one another. For example, in some cases it is desirable to maintain the lower arm generally perpendicular to the upper arm. In this instance, two lengths 10, 10A (FIG. 3) of track can be utilized. One length is along the lower arm. The other length is along the upper arm. In FIG. 3, adjacent ends of tracks 10, 10A generally co-terminate. If desired, however, one adjacent end can extend past the other adjacent end. If after bit 20 is utilized, a portion of a cast remains uncut, then the scissors-like cutting apparatus 30, 32 of FIG. 1 (or another other desired apparatus) can be utilized to finished cutting the cast.

In FIG. 1, foot 31 of tool 30 is shaped and dimensioned generally to fit in, conform to, and move along primary opening 11. In this manner, when foot 31 is slid or otherwise moved along the length of opening 11, opening 11 restricts lateral movement of foot 31 in the directions of arrows A and B and restricts vertical movement of foot 31 upwardly in the direction of arrow C (FIG. 1). Primary opening 11 and foot 31 function in combination to "capture" and restrict the movement of foot 31 while permitting foot 31 to be freely moved along the length of opening 11 while scissors jaw 32 is manipulated about pivot pin 33 in the directions indicated by arrows P in order to cut a cast. If desired, a lower jaw can be provided which also pivots about pin 33 and opposes jaw 32 in the manner that a pair of conventional scissors have a pair of opposing jaws pivoting about a common point.

In FIG. 1, foot 41 of tool 40 is shaped and dimensioned generally to fit in, conform to, and move along primary opening 11. In this manner, when foot 41 is slid or otherwise moved along the length of opening 11, opening 11 restricts lateral movement of foot 41 in the directions of arrows A and B and restricts vertical movement of foot 41 upwardly in the direction of arrow C (FIG. 1). Primary opening 11 and foot 14 function in combination to "capture" foot 41 while permitting foot 41 to be freely moved along the length of opening 11 while saw blade 42 rotates in one of the directions indicated by arrows 43. A slot 40A can be formed in tool 40 so that blade 42 can travel up and down in slot 40A while the blade 42 is cutting the fiberglass cast 14.

In FIG. 4, insert 70 is shaped and dimensioned to generally conform to and to be slidably inserted simultaneously into primary opening 11 and secondary opening 18A. When track 10 is placed on a part of an individual's body and a fiberglass cast 14 is wrapped around track 10, forces acting in the direction of arrows J, K, and L are generated, act against, and tend to deform track 10. Insert 70 functions to maintain the shape and dimension of track 10 and, in particular, of openings 11 and 18A. Maintaining the shape of openings 11 and 18A is important because foot 21 and shaft 22 must freely move along openings 11 and 18A, respectively, when bit 20 is utilized to cut through and remove cast 14. An insert that provides support for track 10 need not have the "inverted T" shape of insert 70 or conform closely to the shape and dimension of openings 11 and 18A. An insert 71 with an oval or circular or other cross-sectional area can function, when inserted in track 10, to provide support and prevent or minimize the deformation of track 10 when forces J, K, or L are applied to track 10. As is illustrated in FIG. 3, track 10 can, if desired, be somewhat pliable along its length such that track 10 will bend downwardly (or upwardly) longitudinally. An insert 70, 71 can similarly be somewhat pliable and bend downwardly (or upwardly) along its longitudinal axis such that track 10 and an insert 70, 71 can—when insert 70, 71 is slidably inserted in openings 11 and/or 18A and extends along (either partially or completely) the length of track 10—bend simultaneously along their longitudinal axes.

An alternate embodiment of the invention is illustrated in FIGS. 5 to 9.

Figures 5, 6:
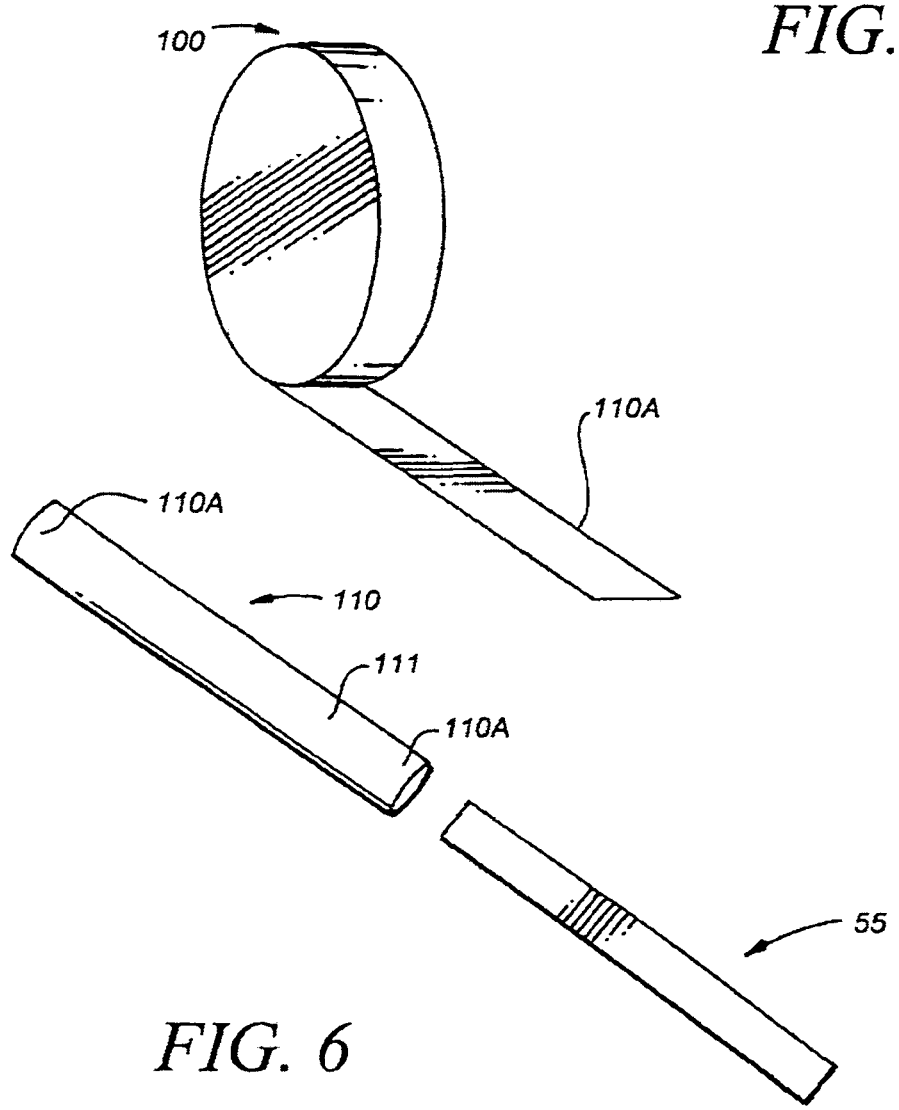
FIG. 5 is a perspective view illustrating a roll of pliable hollow tape utilized in an alternate embodiment of the invention.
FIG. 6 is a perspective view illustrating the mode of operation of the tape of FIG. 5 in conjunction with a support tool in accordance with the alternate embodiment of the invention.

FIG. 5 illustrates a roll 100 of pliable hollow thin-walled guide tubing having a free open end 110A.

As illustrated in FIG. 6, a strip 110 of pliable tubing is cut from roll 100. Strip 110 comprises hollow sleeve 111. Tubing sleeve 111 can, but preferably is not, be elastic. Sleeve 111 includes a pair of free open ends 110A. Consequently, although sleeve 111 is formed from a pliable polymer or other pliable material, sleeve 111 ordinarily will not stretch like a rubber band, or if sleeve 111 does stretch, it will do so only minimally.

FIG. 6 also illustrates a support tool 55 comprised of a strip or rod fabricated from plastic or metal or other material. Tool 55 is substantially rigid but is also pliable in the manner, for example, of a flat thin orthogonal ruler fabricated from a thin strip of stainless steel. The stainless steel ruler can be pliably arcuately bent about a horizontal axis that is perpendicular to the longitudinal axis of the ruler (i.e.; the ruler is not, however, permanently deformed, does not stretch, and when released will spring back and return to its original "flat" orientation in which the ruler lies flat on the flat surface of a table. Further, the stainless steel ruler is generally not pliable and bendable about its longitudinal axis. The ruler typically cannot be arcuately bent about its longitudinal axis without permanently deforming the ruler. If, for example, the opposing longitudinal edges of a one inch wide, one foot long thin stainless steel ruler are squeezed between the thumb and forefinger of a hand (such that the thumb and forefinger are spaced about one inch apart and are directly opposed to one another), the ruler ordinarily cannot be arcuately bent between the thumb and forefinger. The ruler maintains its flat configuration. On the other hand, if one end of the ruler is held by an individual's right hand and the other end of the ruler is held by the individual's left hand, the ruler has a pliability which to a limited extent permits the ruler to be gently twisted (i.e., one end is rotated in a direction opposite the direction of rotation of the other end of the ruler) about the longitudinal axis of the ruler. When the ruler is twisted in this manner, it is not permanently deformed and will tend to spring back or return to its original non-twisted, flat configuration when the twisting forces acting on the ruler are discontinued and the ends of the ruler are released.

The pliability of tool 55 permits it to conform to a certain extent to a person's body while still providing support for sleeve 111. It is possible for tool 55 to be fabricated such that it pliable about its longitudinal axis, particularly as the ruler becomes wider, but such is not a presently preferred embodiment of the invention.

Tool 55 is slidably inserted in pliable sleeve 111 to support and generally maintain the elongate configuration of tubing sleeve 111 while sleeve 111 is mounted on padding 121 that extends around the arm or other body portion of an individual. Tool 55 is important in the practice of the invention because it tends to prevent sleeve 111 from bunching up or wrinkling when cast material is being applied over sleeve. The objective is to keep sleeve 111 in a smooth, uniform, flat configuration while a cast is being applied over sleeve 111.

Figure 7:
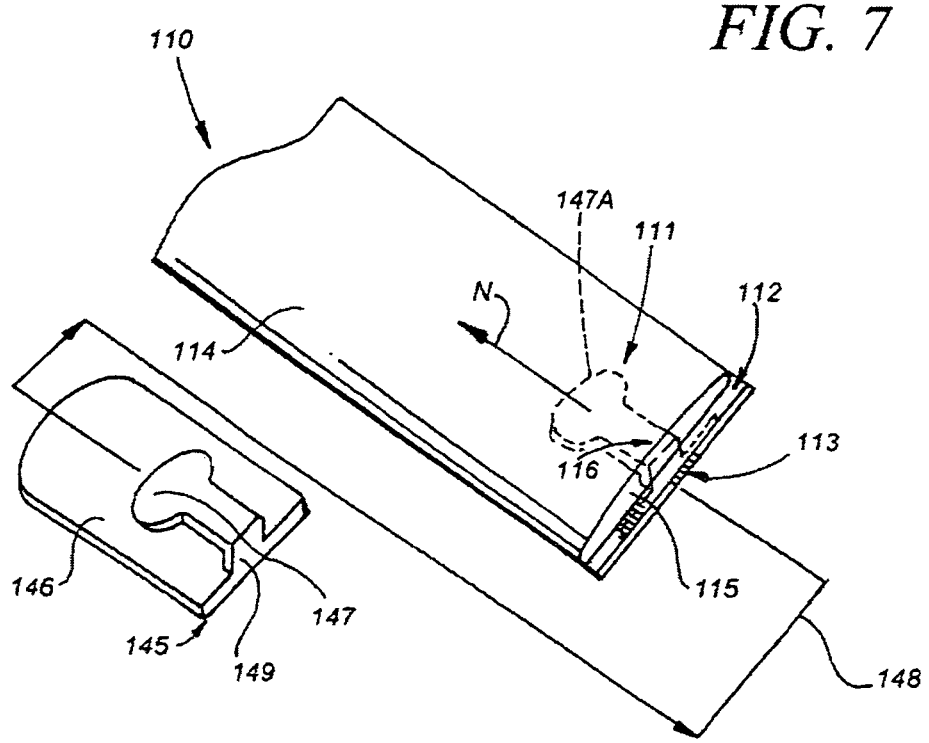
FIG. 7 is an enlarged perspective view further illustrating a section of the tape of FIG. 5.

The strip 110 is further depicted in FIG. 7 and illustrates the top 114 and bottom 115 of hollow elongate polymer sleeve 111. Foam strip 112 is glued or otherwise adhered to the exterior of bottom 115. A layer 113 of contact adhesive is formed on the bottom of foam strip 112 and is covered by a protective peelable removable strip (not shown) of wax paper or other material. This peelable strip is removed from adhesive layer 113 prior to applying sleeve 111 to the padding 121 on the arm (or leg or other body portion) 120 of a patient.

Figure 8:
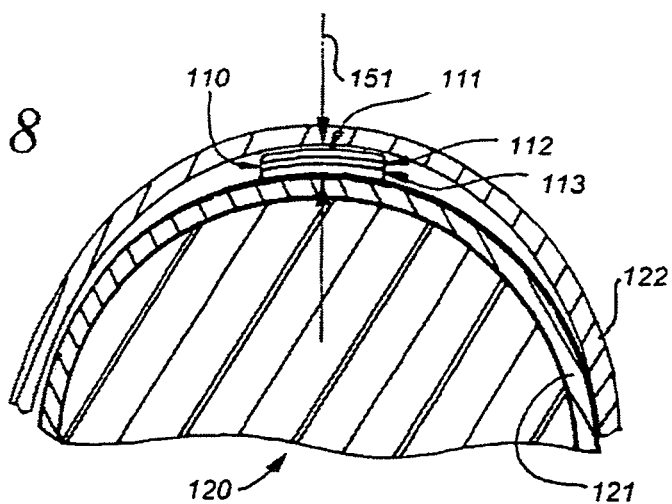
FIG. 8 is a perspective view further illustrating the mode of operation of the tape of FIG. 5.
Figure 9:
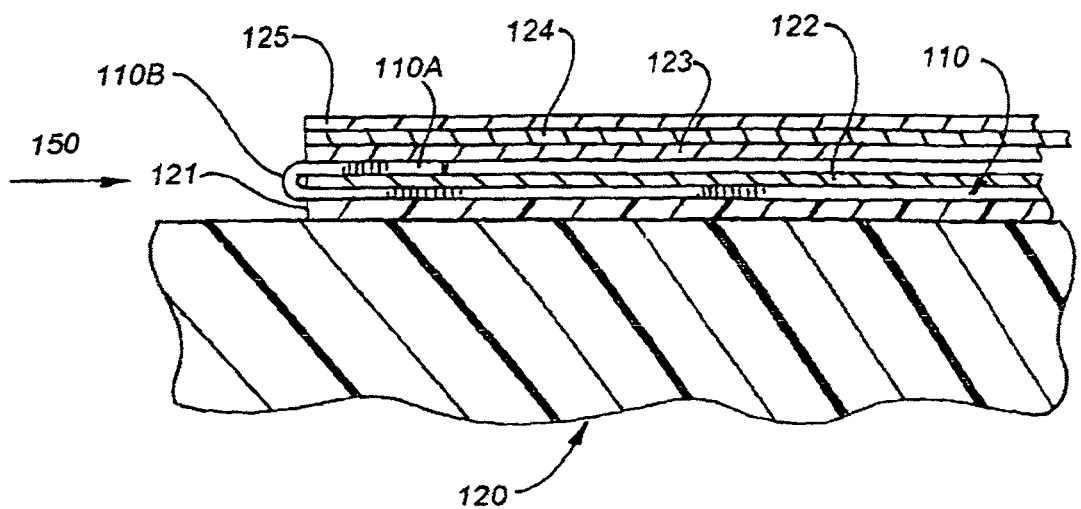
FIG. 9 is a side section view illustrating the mode of operation of the tape of FIG. 5.

FIGS. 8 and 9 illustrate the mounting of pliable substantially non-elastic strip 110 during the application of a cast to the arm 120 of an individual. After a physician has, if necessary, appropriately aligned and set a broken bone, padding 121 is wrapped around arm 120. Antiseptic can, if desired, be applied to the surface of arm 120 prior to applying padding 121. A sleeve 111 of appropriate length is cut. The length of sleeve 111 is, as will be apparent below, greater than the length of the cast that is to be applied. Tool 55 is slidably inserted in sleeve 111. Tool 55 preferably, but not necessarily, extends along the entire length of sleeve 111.

The protective peelable backing covering the layer 113 of contact adhesive is removed, and sleeve 111 is mounted on padding 121 such that contact adhesive layer 113 adheres to padding 121. The use of force to press sleeve 111 against padding 121 is minimized to minimize discomfort to the patient. Each of the free ends 110A of sleeve 111 extends outwardly beyond the ends of padding 121. Once sleeve 110 is in place on padding 121, tool 55 can, if desired, be slidably removed from sleeve 111.

The first layer 122 of fiberglass is wrapped around and over padding 121 and sleeve 111. Tool 55 must then, if not already removed from sleeve 111, be slidably removed from sleeve 111. The free ends 110A of sleeve 111 are wrapped up and over the first layer 122 of fiberglass and a second layer 123 of fiberglass is wrapped over and around the first layer 122 of fiberglass. The second layer 123 extends over free ends 110A and fixes them in place in the manner illustrated in FIG. 17. As a result, an elbow 110B or bend is formed at each end of sleeve 111. When the time comes to remove the cast, elbow 110B is cut to form an open end in sleeve 111 so that the foot 136 (FIG. 9) of the cutting tool can be inserted in the open end of and slide along sleeve 111. Additional layers 124 and 125 of fiberglass are applied and extend over and around fiberglass layer 123. The fiberglass layers 122 to 125 are permitted to harden to complete the application of the cast.

In an alternate embodiment of the invention, padding 121 extends a distance along arm 120 that is generally equivalent to the length of sleeve 111; however, the fiberglass layers extend a distance along arm 120 that is less than the distance which padding 121 (and sleeve 111) extends. Since the distance along arm 120 that the fiberglass extends is less than the distance along the arm 120 that sleeve 111 extends, this still permits the free ends 110A of sleeve 111 to be wrapped up and over fiberglass layer 122 in the manner illustrated in FIG. 9.

In a further embodiment of the invention, the free ends of sleeve 111 are not wrapped up and over the first layer of fiberglass in the manner describe above. Instead, after fiberglass layer 122 is applied, the free ends are cut off so that the ends of sleeve 111 generally co-terminate with the ends of the layer 122. Each end of sleeve 111 is sealed using the closure 145 illustrated in FIG. 7. The tombstone-shaped foot 146 of each closure 145 is inserted in an end of sleeve 111 in the manner indicated by arrow 148 in FIG. 1. Clip 147 extends upwardly and then over the top of layer 122 in the manner suggested in FIG. 7. Layer 122 is not depicted in FIG. 7, but clip 147 would, however, extend over the top of layer 122 in the same manner it extends over the top 114 of sleeve 111 in FIG. 7. The subsequent layer of fiberglass 123 extends over and secures clip 147 (and insert 145) in place. When the time arrives to remove the cast, arm 149 is cut and foot 146 is pulled out from the end of sleeve 111 so that tracking foot 136 can be inserted in sleeve 111 in the manner described below.

Once the fiberglass cast has been worn a time sufficient for the bone to heal, or in the event there is another reason to remove the cast, the cast is removed.

First, scissors or another cutting tool is used to cut through the loop 110B at each end of the cast. This produces an opening at each end of the portion of sleeve 111 that extends intermediate padding 121 and fiberglass layer 122.

Figure 14:
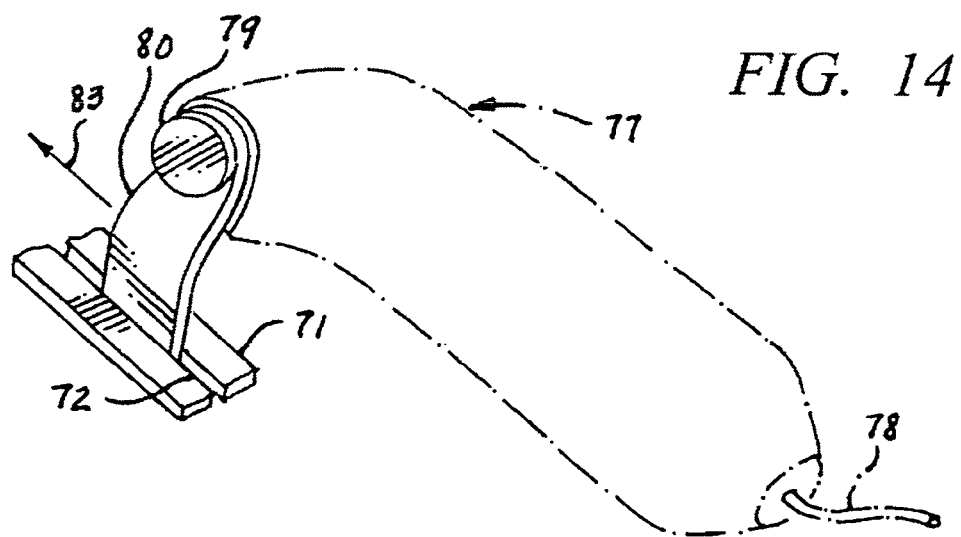
FIG. 14 is a perspective view illustrating the mode of operation of an alternate embodiment of the invention.

Second, the oscillating tool of FIG. 14 is utilized to cut through the cast.

Motive power to operate the motor in the tool of FIG. 14 can be supplied by a battery mounted in the tool housing 77, by electricity flowing through an electrical cable 78, etc.

After loop 110B is cut, the tool of FIG. 14 is manually grasped in the orientation pictured in FIG. 14 and blade 80 moves along the slot formed in the top of track 10 in the direction of arrow 83 to cut through the cast.

As would be appreciated by those of skill in the art, FIG. 9 illustrates the insertion of a first sleeve 111 on one side of arm 120. Ordinarily another second sleeve 111 is similarly inserted on the opposite side of arm 120 (or of a leg or other part of the body) and is parallel to the first sleeve 111 so that when the time comes to remove the cast, the cast is cut apart along two opposing sides of the cast.

Sleeve 111 must, in accordance with the invention, have several important properties.

First, the sleeve 111 must be pliable and bend in the same manner that a strip of conventional flat Christmas ribbon is pliable and bends this in order to permit the sleeve 111 to generally conform to a patient's body.

Second, the sleeve must not be elastic and readily deform. In this sense, sleeve 111 is again similar to a piece of conventional elongate flat Christmas ribbon because such ribbon normally is not even though it readily bends around the corners of a Christmas package—elastic; the ribbon does not readily stretch longitudinally or transversely. If the sleeve 111 were elastic and readily deformed, it could allow the leading edge of foot 136 to catch, deform, and bind sleeve 111.

Third, when the sleeve 111 is fabricated from a polymer, the polymer must have a strength sufficient to minimize the likelihood that end 74 (FIG. 12) or tool 55 can puncture the sleeve. It is preferred that the polymer have a width of at least 2 mils, preferably 3 mils, and most preferably at least 4 mils.

Fourth, it is important that sleeve 111 not lose its physical properties when heat is generated in the cast while the fiberglass cures. Consequently, the sleeve must not soften, melt, or become elastic in the event the sleeve is heated up to a maximum temperature of 130 degrees F., more preferably in the event the sleeve is heated up to a maximum temperature of 140 degrees F., and most preferably in the event the sleeve is heated up to a maximum temperature of 150 degrees F. A fiberglass cast can generate heat while it cures and hardens. It is believed that the temperature in the cast can, depending on conditions, exceed fifty degrees centigrade while the cast cures.

Fifth, the sleeve 111 must permit the lower leg 75 of guide 70 to slide freely along the sleeve when guide 70 and the tool of FIG. 14 are used to remove a cast. To this end, sleeve 111 can, if desired, be fabricated from a polymer, metal, or other material that includes an interior surface having a low coefficient of friction so that leg 75 readily freely slides along the interior of sleeve 111. Or, the interior of sleeve 111 can be coated with a material like Teflon™ that has a low coefficient of friction. Forming the interior surface of sleeve 111 from a "sticky" polymer which tends to adhere to leg 75 or foot 21 or tool 55 normally is not acceptable. Leg 75 preferably does not stick or adhere to the material comprising strip 111.

Sixth, the overall thickness, indicated by arrows 151 in FIG. 8, of strip 110 when top 114 is flat against bottom 115 is important. If the strip is too thick, the fiberglass layers can squeeze strip 110 and produce pressure which is uncomfortable to a patient, especially in the long term. The thickness 151 is no more than one-fourth of an inch, preferably no more than one-eighth of an inch, and more preferably no more than $3/32$ of an inch, and most preferably no more than $1/16$ of an inch. This thickness 151 includes sleeve 111, foam layer 112, and the adhesive layers. It does not include the protective removable backing strip that covers the adhesive layer 113. In an alternate embodiment of the invention, a foam layer 112 is not utilized and is not secured to sleeve 111.

Figure 11:
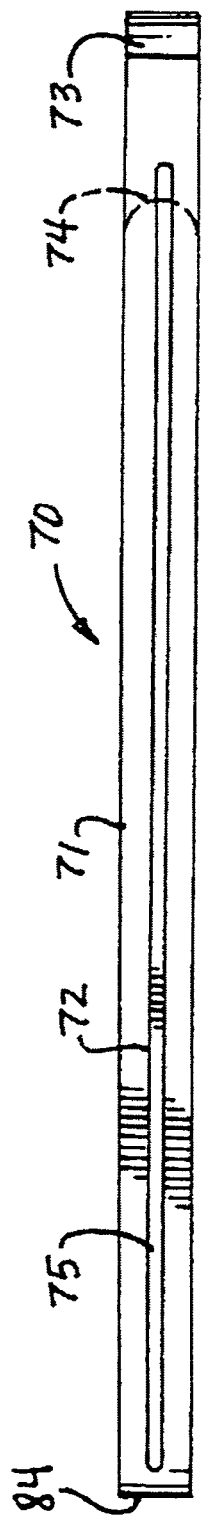
FIG. 11 is a top view illustrating a guide utilized in the practice of the invention.
Figure 12:
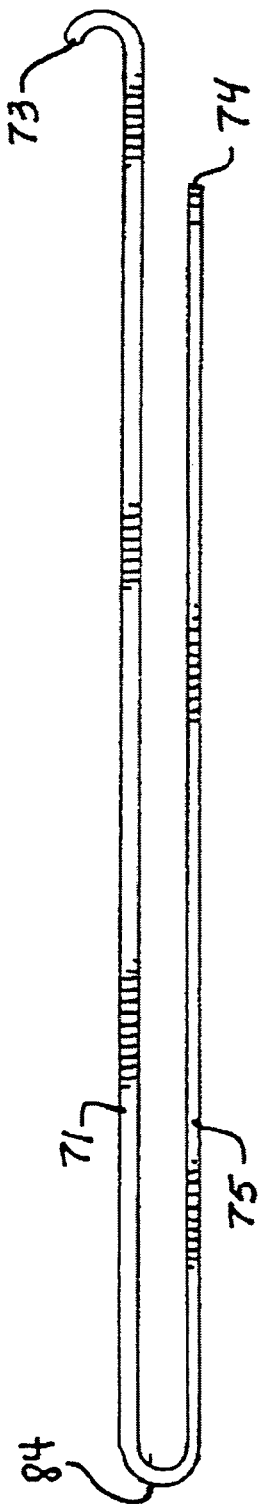
FIG. 12 is a side view illustrating the guide of FIG. 11.

FIGS. 11 and 12 illustrate a guide 70A utilized in an alternate embodiment of the invention. Guide 70A includes a pair of spaced apart parallel legs 71A and 75 interconnected by arcuate end 84. Upper leg 71A includes a guide slot 72 extending along at least a portion of the longitudinal axis of leg 71A. Lower leg 75 generally has the same shape and dimension as upper leg 71A, but lower leg 75 comprises a solid generally orthogonal member which does not have a slot cut through lower leg 35. Consequently, in the top view of FIG. 11 a portion of leg 75 is visible through (and beneath) slot 72.

Handle 73 is connected to one end of upper leg 71A. Lower leg 75 includes a rounded end 74 spaced apart from and beneath handle 73 of upper leg 71A.

Figure 13:
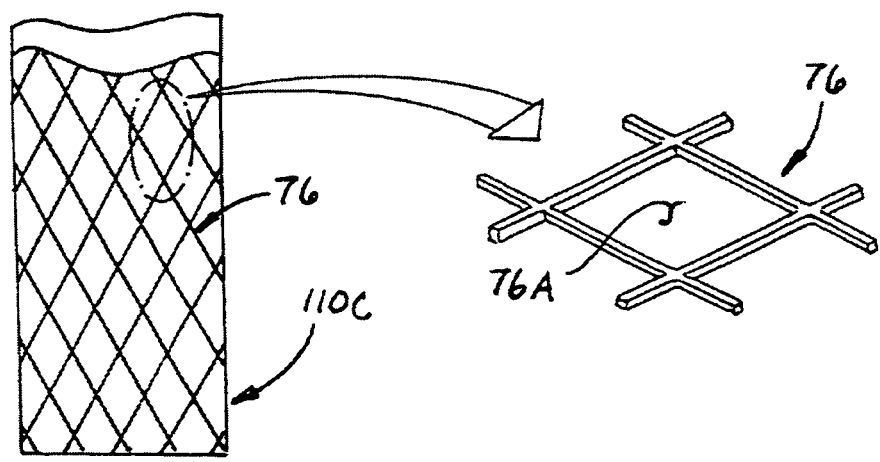
FIG. 13 is a top view illustrating an alternate embodiment of the tape utilized in the practice of the invention.

In one embodiment of the invention, a hollow strip 110C includes a mesh 76 (FIG. 13) on its upper surface. The mesh 76 functions to interlock with fiberglass which is wrapped around the arm or other portion of an individual's body on which a cast is being applied. When fiberglass is initially wrapped around an individual's arm and over mesh 76, the fiberglass is wet and pliable and tends to drape, or flow, into openings 76A so that when the fiberglass hardens, the mesh 76 is interlocked with fiberglass which extends into openings 76A. The interlocking of mesh 76 and fiberglass is important because it functions to help maintain strip 110C in fixed position, which is, as will be described below, important when a guide 70 is utilized to remove a cast. In an alternate embodiment of the invention, a strip 110, 110C does not include mesh 76; however, strip 110, 110C is preferably fabricated of a material (or some other material which is coated on or adhered to the top of strip 110, 110C) which adheres to fiberglass which is wrapped around and over strip 110, 110C and which, when the fiberglass hardens, functions in tandem with the fiberglass to maintain strip 110, 110C substantially in fixed position with respect to the fiberglass.

Mesh 76 comprises a woven, knit, knotted, or otherwise formed material having a weblike pattern of generally open texture with openings 76A that can be, but are not necessarily, evenly spaced.

FIG. 14 illustrates an oscillating tool including a housing 77, connector 79, blade or attachment 80, and electrical cord for delivering electricity to a motor (not visible) mounted in housing 77. The motor functions to oscillate and move attachment 80 through a narrow arc, typically about a three degree arc, at speeds typically in the range of 3,000 to 25,000 opm (oscillations per minute). Connector 79 removably secures attachment 80 on housing 77. The shape and dimension of attachment 80 can vary as desired. One or more of the peripheral edges of attachment 80 typically includes a plurality of small cutting teeth.

Figure 10:
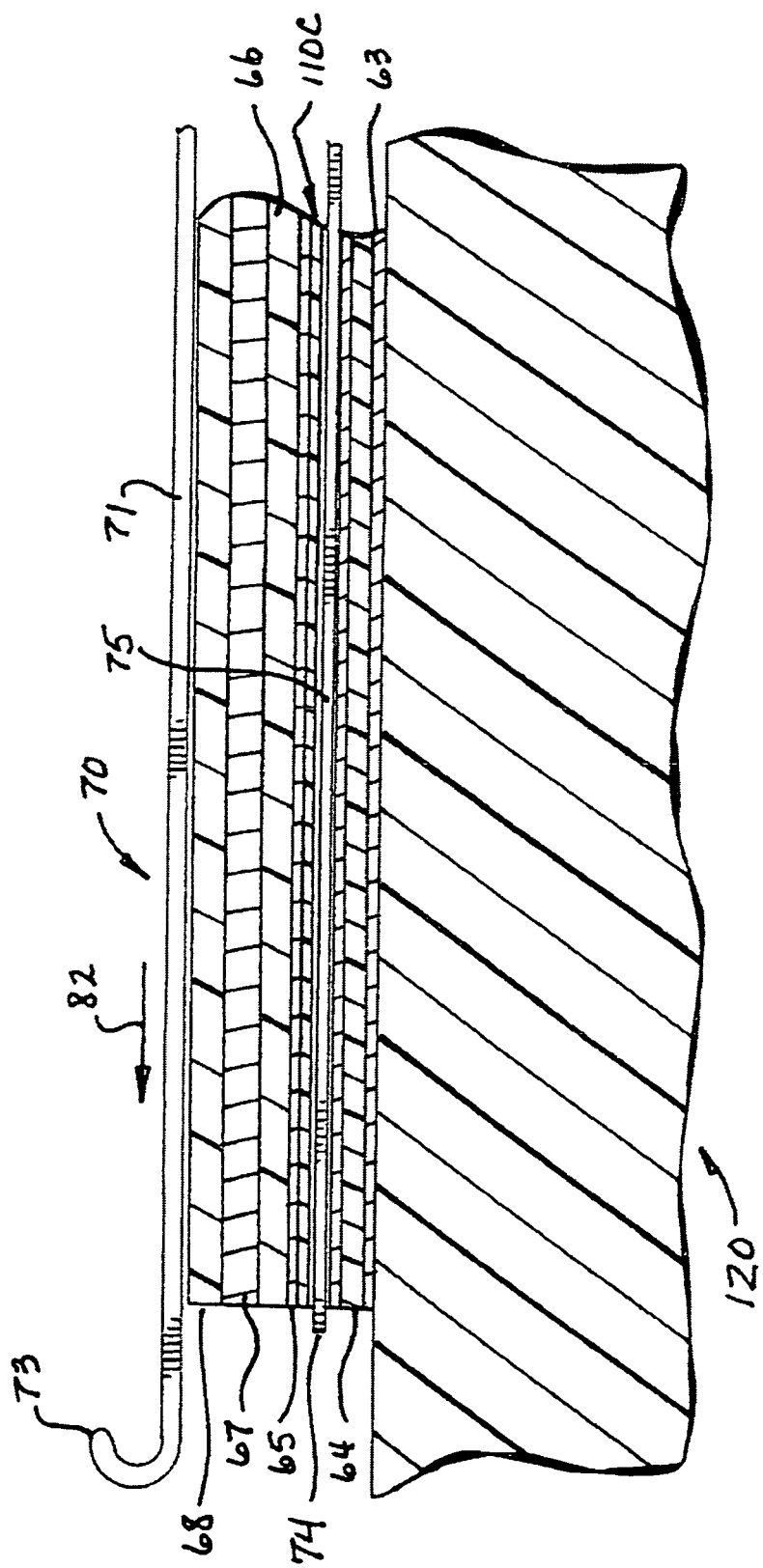
FIG. 10 is a side section view illustrating the mode of operation of another embodiment of the invention.

FIG. 10 illustrates an alternate embodiment of the invention in which pliable substantially non-elastic hollow strip 110C is incorporated during the application of a cast to the arm 120 of an individual. After a physician has, if necessary, appropriately aligned and set a broken bone, a thin elastic nylon sleeve 63 is mounted on and circumscribes arm 120, after which cotton or other fabric padding 64 is wrapped around arm 120. Antiseptic can, if desired, be applied to the surface of arm 120 prior to applying sleeve 63 and padding 64. A strip 110C of appropriate length is cut. The length of strip 110C is generally equal to or longer than the length of the cast that is to be applied. Strip 110C includes a layer of contact adhesive on the exterior bottom surface of the hollow polymer sleeve (which sleeve is comparable to sleeve 111 in strip 110), which sleeve comprises the center portion of strip 110C; and, includes a strip of wax paper or other material which extends along and covers the contact adhesive and which can be peeled off the contact adhesive to expose the adhesive. Strip 110C also includes a layer of mesh 65 fixedly glued or otherwise adhered to the exterior top surface of the hollow polymer sleeve which comprises the center portion of strip 110C.

Tool 55 is manually grasped and slidably inserted in the polymer sleeve of strip 110C. When tool 55 is full inserted in the polymer sleeve, tool 55 preferably, but not necessarily, extends along the entire length of the sleeve and extends out at least one end of the polymer sleeve. The portion of tool 55 which extends out one end of the polymer sleeve facilitates removing tool 55 from the sleeve.

The protective peelable backing covering the layer of contact adhesive on the bottom of the hollow polymer sleeve is removed, and strip 110C is mounted on padding 64 such that the contact adhesive layer (not visible in FIG. 10) adheres to padding 64. The use of force to press strip 110C against padding 64 is minimized to minimize discomfort to the patient. Each of the open ends of the hollow polymer sleeve in strip 110C generally coterminates with the ends of padding 64, although the open ends can, if desired extend outwardly past the end of padding 64 on arm 120, or, can be located within or inset from the points at which padding 64 terminates. Once strip 110C is in place on padding 64, the portion of tool 55 which extends out one end can, if desired, be manually grasped and tool 55 can be slidably removed from strip 110C. Alternatively, tool 55 is left in strip 110C until the layers of fiberglass have been wrapped around arm 120 and strip 110C, after which tool 55 is removed from strip 110C.

The first layer 66 of fiberglass is wrapped around and over padding 64 and strip 110C. A portion of the first fiberglass layer 66 extending over the top of the hollow polymer sleeve interlocks with openings 76A in the mesh layer 65 which extends along the exterior of the top of the polymer sleeve in strip 110C. When layer 66 hardens it, along with the contact adhesive between the bottom of the hollow polymer sleeve and padding 64, generally fixedly secures and fixes strip 110C in position between layer 66 and padding 64. Such fixation of strip 110C is important because it reduces the likelihood that leg 75 will, when inserted in the polymer sleeve of strip 110C, tear or bind with the polymer sleeve. In the event the top of the hollow polymer sleeve is not provided with mesh layer 65, then the top of the hollow polymer sleeve preferably is made from a material(s) which will adhere to fiberglass such that when fiberglass is wrapped about strip 110C and harden, the top of the hollow polymer sleeve adheres to the hardened fiberglass to secure strip 110C in fixed position against the fiberglass.

A second layer 67 of fiberglass is wrapped over and around the first layer 66 of fiberglass. One or more additional layers 68 of fiberglass are applied and extend over and around fiberglass layer 67. The fiberglass layers 66 to 68 are permitted to harden to complete the application of the cast. A plug 145 or other filler is placed in each end of the hollow polymer sleeve and is securely taped in position. Any other desired method can be used to close temporarily the ends of the hollow polymer sleeve.

Once the fiberglass cast has been worn a time sufficient for the bone to heal, or in the event there is another reason to remove the cast, the cast is removed.

First, at least one end of the hollow polymer sleeve is opened by removing the plug 145 in the end of the sleeve.

Second, handle 73 of guide 70A is grasped and tool 70A is manually manipulated to insert end 74 of lower leg 75 of guide tool 70A in the open end of the hollow polymer sleeve and to push leg 75 through and along substantially the entire length of the hollow polymer sleeve (and thereof of the strip 110C) in the direction of arrow 82 (FIG. 10). After leg 75 is pushed into the hollow polymer sleeve, the guide 70 is positioned as depicted in FIG. 10 with the upper leg 71A of guide 70 extending along the outer surface of the cast and lower leg 75 extending through strip 110C.

Third, the oscillating tool of FIG. 14 is utilized to cut through the cast. Namely, housing 77 is manually grasped, and blade 80 is used (while the tool is being powered with electricity) to track along guide slot 72 and cut through the cast in the manner illustrated in FIG. 14. While blade 80 cuts through the cast and tracks along slot 72, the distal or outer end of blade 80 tracks along or near lower leg 75. Lower leg 75 prevents blade 80 from cutting through padding 64 and sleeve 63 and contacting a patient's epithelial tissue.

Figure 18:
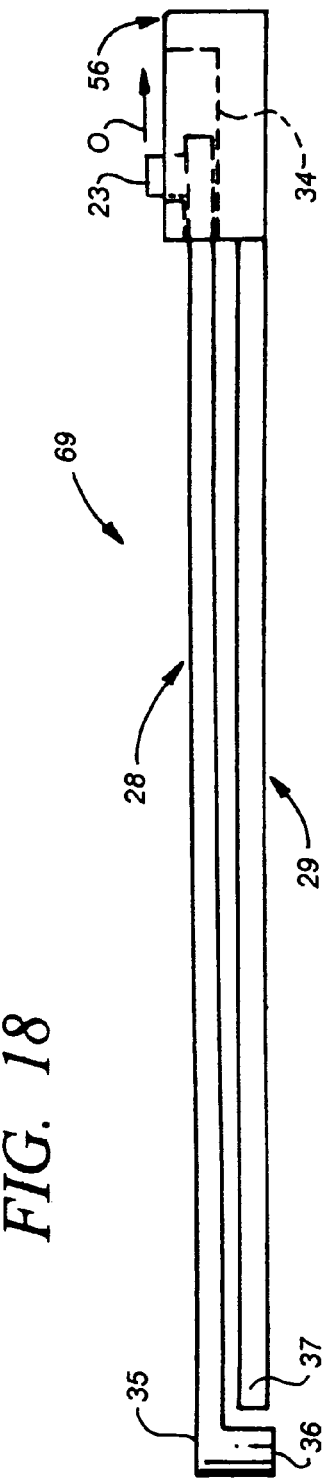
FIG. 18 is a top view illustrating the guide assembly utilized in FIG. 15.
Figure 19:
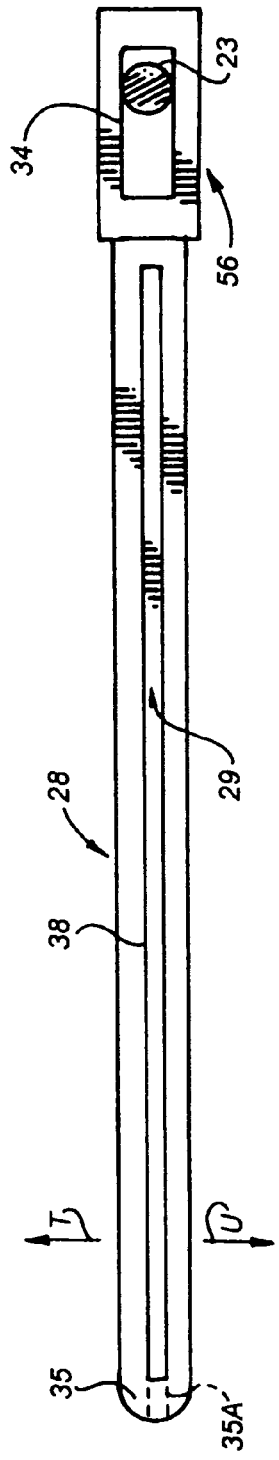
FIG. 19 is a side view illustrating the guide assembly of FIG. 18 and the mode of operation thereof.

The guide 70A utilized in one embodiment of the invention is illustrated in FIGS. 11 and 12. FIGS. 18 and 19 illustrate a similar guide which is generally indicated by reference character 69. Guide 69 includes an elongate lower leg 29 having a distal arcuate end 37. Leg 29 comprises an elongate solid strip which does not have a slot extending through leg 29. The proximate end of leg 29 is fixedly anchored in handle 56.

Guide 29 also includes an elongate upper leg 28 having an elongate slot 38 extending through leg 28.

The distal end 35 of leg 28 includes a hollow cup 36 extending downwardly therefrom. Cup 36 is shaped and dimensioned to fit over and enclose and prevent the lateral movement of end 37 of leg 29.

The proximate end of leg 28 is slidably received in slot or opening 34 formed in handle 56. Cylindrical member 23 depends upwardly from the proximate end of leg 28. The proximate end of leg 28 (and therefor leg 28) is manually displaced in the direction of arrow D by placing a finger on top of member 23 and moving member 23 in the direction of arrow D to the position illustrated in FIG. 19. When leg 28 is in the position illustrated in FIG. 19, cup 36 encloses end 37 and prevents the lateral movement of leg 28 in the direction of arrow U or T away from registration with leg 29. In FIG. 19, leg 28 is parallel to and in registration with leg 29. The width of leg 29 is equal to the width of leg 28. Consequently, in FIG. 19 the only portion of leg 29 that is visible is the portion of leg 29 that can be seen through slot 38 of leg 28.

Maintaining leg 28 in registration with leg 29 is important in the practice of the invention because a bit or saw blade or other cutting member that is traveling along slot 38 bears against leg 29 and leg 29 protects the arm or other body part that is beneath leg 29. If leg 28 moves out of registration with leg 29, it is possible that a bit or saw blade will no longer move along leg 29 and will instead be able to contact and injure the tissue of an individual.

In use of guide 29, when a cast needs to be removed, guide 29 is oriented in the configuration shown in FIG. 18. Leg 29 is slidably inserted in one end of a polymer sleeve 111 and pushed through sleeve 111 until end 37 emerges from the other end of sleeve 111. Member 23 is then manually slidably displaced in the direction of arrow D to the position illustrated in FIG. 19 so that cup 36 encloses end 37 of leg 29. Tool 59 is then utilized in the manner described below to cut through cast 57 and form slot 58 in cast 57.

Figure 15:
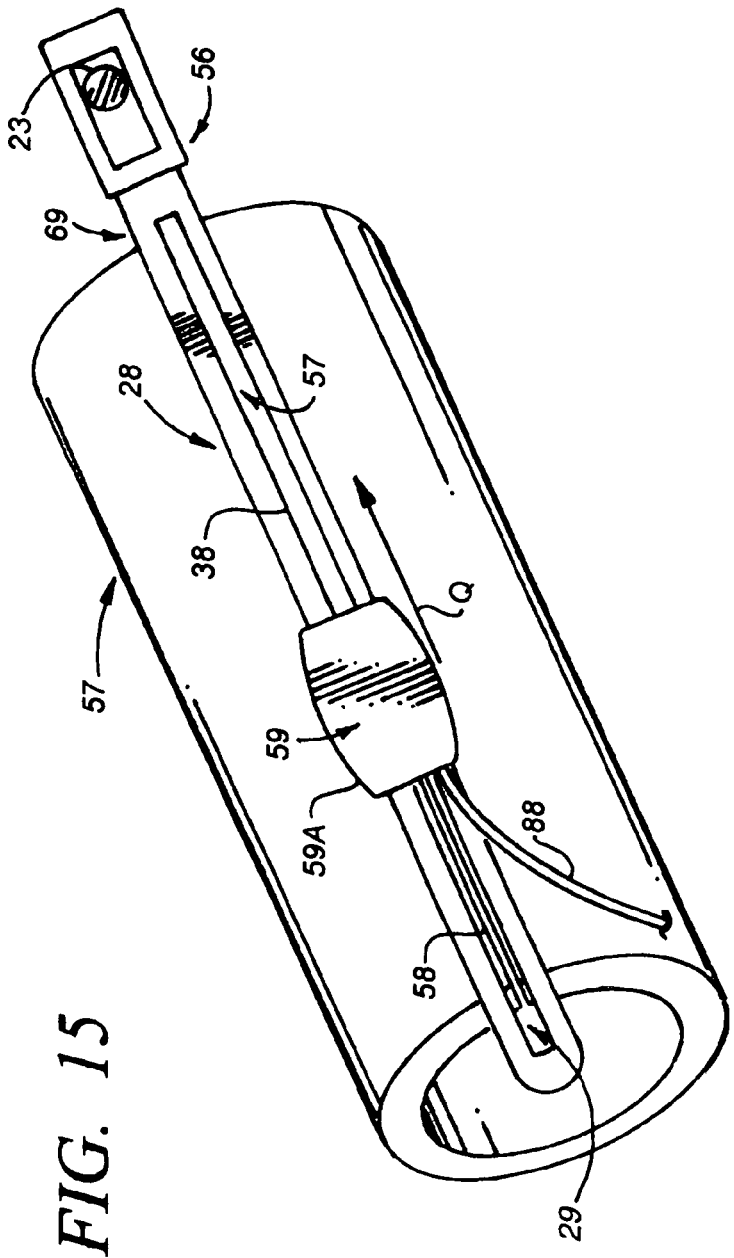
FIG. 15 is a perspective view illustrating the mode of operation of still another embodiment of the invention.

Accordingly, in order for guide 29 to achieve the orientation illustrated in FIG. 15, guide 29 was first oriented in the manner illustrated in FIG. 18 and the lower leg 29 of guide 69 was slidably inserted in a polymer sleeve 111 after the ends of sleeve 111 were opened to permit leg 29 to extend into and through sleeve 111 in the manner depicted in FIG. 15. Further, after leg 29 was slidably inserted in the ends of polymer sleeve 111, member 23 was manually slidably displaced in the direction of arrow D (FIG. 18) to place guide 29 in the orientation illustrated in FIG. 19.

As would be appreciated by those of skill in the art, in FIG. 15 a strip 110, 110C (not visible in FIG. 15) including the polymer sleeve 111 was inserted in cast 57 when cast 57 was being formed or constructed on the arm or other portion of an individual's body. The strip 110, 110C was inserted in cast 57 in the manner described earlier herein with respect to FIGS. 5 to 9 or with respect to FIG. 10. The patient's arm or other limb encircled by cast 57 is not, for the sake of clarity, illustrated in FIG. 15.

Figure 16:
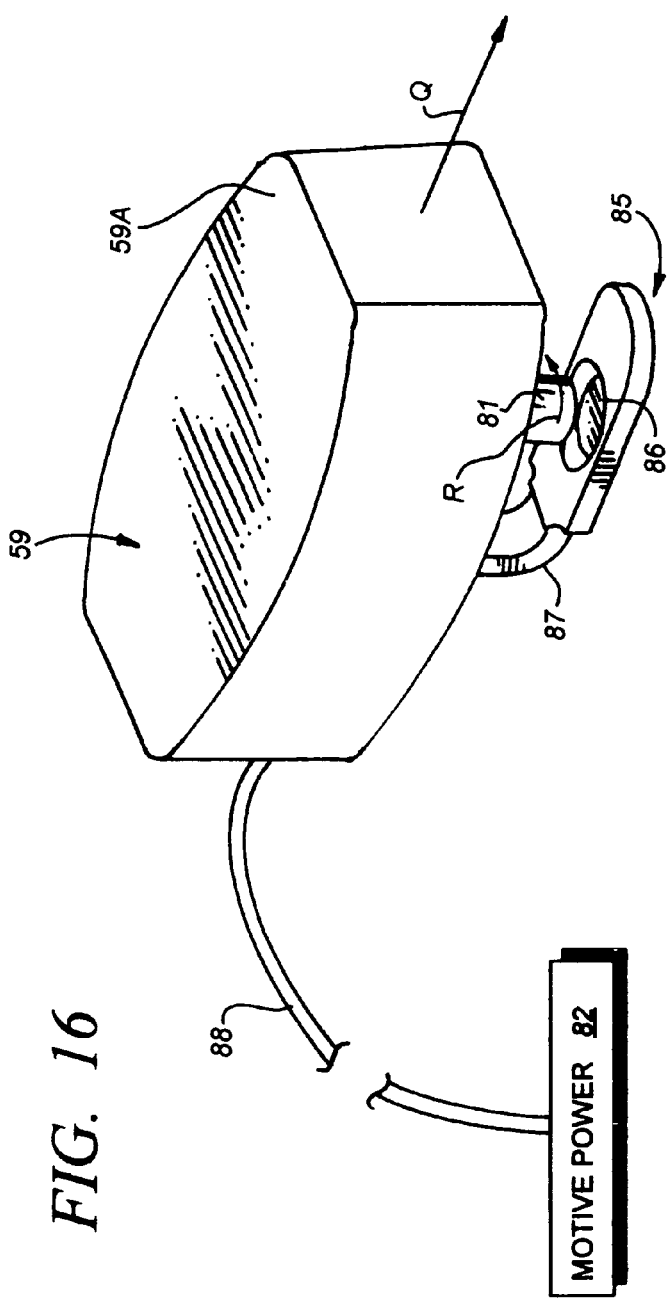
FIG. 16 is a perspective view illustrating additional construction details of the cast cutting apparatus illustrated in FIG. 15.

Tool 59 is illustrated in more detail in FIG. 16 and includes a housing 59A. Bit 81 is rotatably mounted in housing 59A. Bit 81 is shaped and dimensioned like a router bit or any other desired bit that will cut through a cast 57 to form a slit 58 when tool 59 is pushed in the direction of arrow Q (FIG. 15).

Cable 88 extends from housing 59A to a motor or other motive power unit 82 that functions to rotate cable 88. Rotating cable 88 powers a gear assembly in housing 59A that in turn rotates bit 81.

While any desired means and construct can be utilized to provide motive power to rotate bit 81 or a saw blade or another cutting tool in tool 59, the use of cable 88 and a motive power unit 82 remote from tool 59 is a preferred embodiment of the invention for several reasons.

First, separating motive power unit 82 from tool 59 significantly reduces the weight of tool 59 and makes it easier to use and control tool 59.

Second, separating motive power unit 82 from tool 59 reduces the noise produced by tool 59 when it is being used to cut through a cast 57. Reducing the noise level is particularly useful when a cast 57 is being removed from a young child.

Third, the use of a rotating cable and gearing assembly in combination with a rotating bit is a relatively simple mechanical construction.

Fourth, the use of cable 88 and a remote motive power unit 82 also makes it easier to manipulate tool 59 because it enables the size and weight of tool 59 to be minimized.

Foot 85 is fixedly attached to housing 59A by arm 87. Well or depression 86 formed in foot 85 facilitates the gathering and removal of shavings produced when bit 81 cuts cast 57. Foot 85 is shaped and dimensioned to fit into and slide along sleeve 111. In one embodiment of the invention, the interior surface of sleeve 111 is coated with Teflon™ or another friction reducing composition.

Foot 85 normally is inserted in sleeve 111 after leg 29 is inserted in sleeve 111 and before leg 28 is moved in the direction of arrow D to the position illustrated in FIG. 19. An opening 35A (FIG. 19) is preferably formed through end 35 and cup 36 to slidably receive arm 87, to permit arm 87 to slide into slot 38, to permit foot 85 to pass beneath leg 28, and to permit foot 85 to initially slide into sleeve 111. After arm 87 and foot 85 are so positioned, leg 28 is moved in the direction of arrow D to the position illustrated in FIG. 19. Once leg 28 is so positioned, motive power 82 is activated to rotate bit 81, and housing 59A is manually grasped and pushed in the direction of arrow Q (FIGS. 15 and 16) in order to permit rotating bit 81 to travel along slot 38 and to cut a slit 58 through cast 57. Housing 59A is pushed in the direction of arrow Q until slit 58 extends the entire length of cast 57. Guide 69 and tool 59 are separated from cast 57 and are then utilized to make a similar cut on the opposing side of cast 57 so that the resulting cast halves can be removed from the arm of the patient.

In an alternate embodiment of the invention, foot 85 and neck 87 are each sized to fit downwardly through slot 38 so that opening 35A need not be formed in leg 28.

Figure 17:
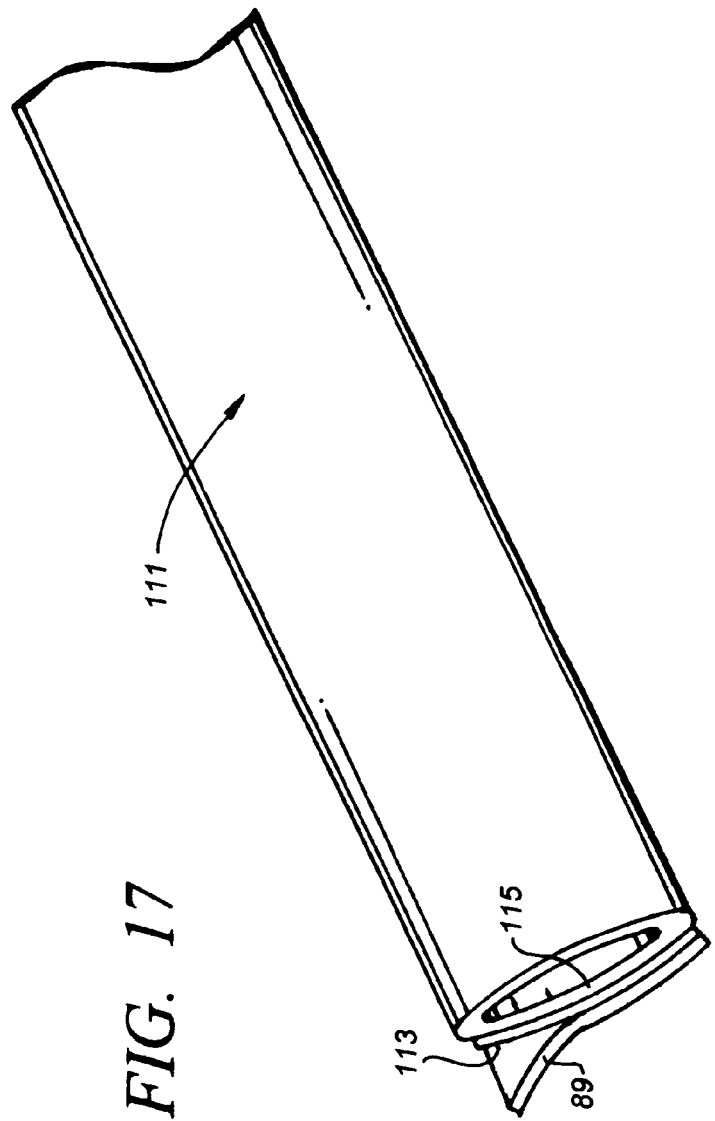
FIG. 17 is a perspective view illustrating an alternate construction of the pliable, thin, polymer tube utilized in the practice of the invention.

FIG. 17 illustrates a protective peelable removable strip 89 of wax paper or some other material which covers and protects the layer 113 of contact adhesive on the bottom of sleeve 111. Peelable strip 89 is removed from layer 113 prior to applying sleeve 111 to padding 121 on the arm 120 or other body portion of a patient.

Figure 24:
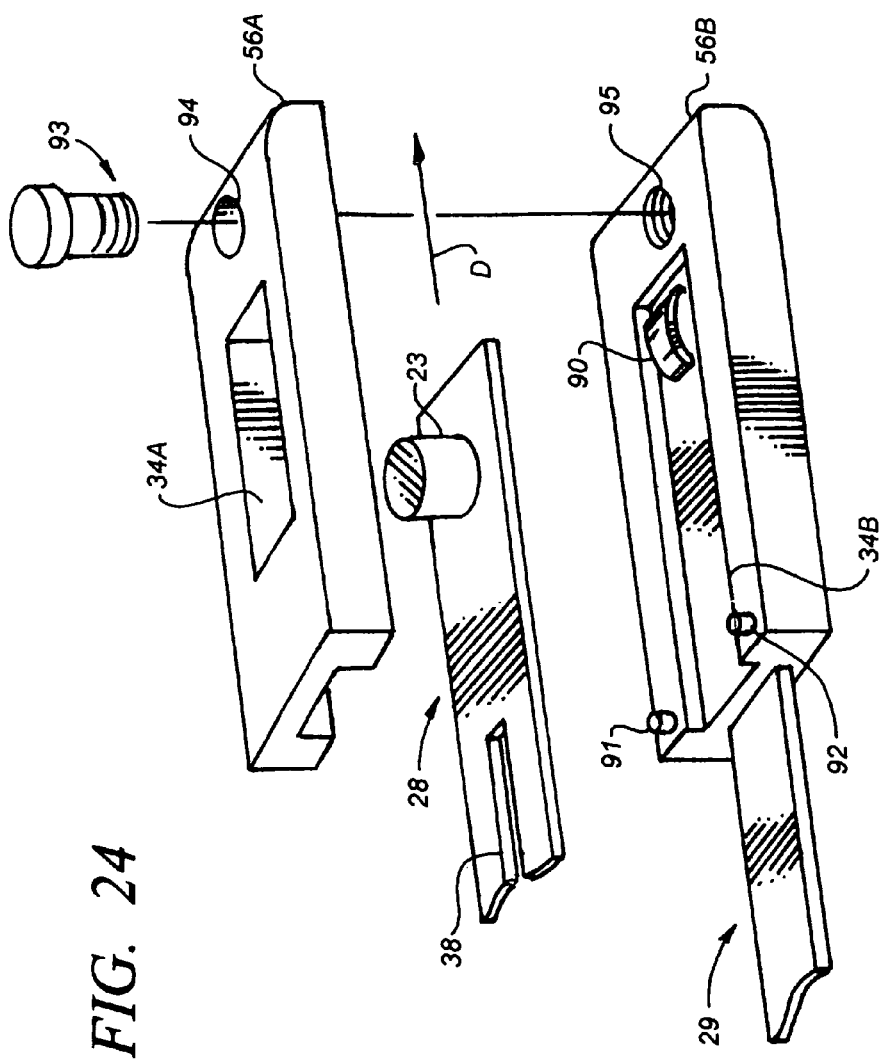

The structure of guide 69 is illustrated in more detail in FIG. 24 where handle 56 includes top portion 56A and bottom portion 568. Upstanding nipples 91 and 92 depend from and are fixedly attached to bottom portion 568. Each nipple 91, 92 is received by and seats in an opposing aperture (not visible) formed in top portion 56A. Externally threaded fastener 93 extends through aperture 94 in top portion 56A and turns into internally threaded aperture 95 in bottom portion 568. Upstanding leaf spring 90 is mounted on the floor of opening 34. Opening 34 includes upper portion 34A and lower portion 348. In FIG. 24, leg 28 is in the same position as is illustrated in FIG. 18, and leg 28 does not contact leaf spring 90. When, however, leg 28 is moved in the direction of arrow D to the position illustrated in FIG. 19, the bottom of leg 28 slides over and downwardly compresses spring 90. When spring 90 is compressed in this manner, it generates compressive frictional forces against the bottom of leg 28 which tend to hold leg 28 in the position illustrated in FIG. 19. At the same time, however, these frictional forces are not sufficient to prevent leg 28 from being moved manually (by pushing member 23) in a direction opposite that of the direction indicated by arrow D to return leg 28 to the position illustrated in FIG. 18.

As discussed earlier herein, maintaining leg 28 in registration with leg 29 is important and is preferred in the practice of the invention. In FIGS. 18 and 19, cup 36 is used to capture end 27 to help maintain legs 28 and 29 in registration with each other. An alternate construction for achieving the same function is illustrated in FIG. 20.

In FIG. 20 a cup 36 is not formed on the distal end 35 of leg 28. Instead, member 39 is fixedly attached to and outwardly depends from end 35. The cylindrical throat 45 of member 39 has a diameter smaller than that of the cylindrical head 44 of member 39. Throat 39 is shaped to slide into slot 47 formed in the distal end of leg 29. The diameter of head 44 is too large to slide into slot 47. Head 44 will fit into and through aperture 46. When leg 28 is in the position illustrated in FIG. 18, head 44 can be pushed downwardly and completely through aperture 46 such that when leg 28 is moved to the position illustrated in FIG. 19, neck 45 slides into slot 47 and head 44 slides underneath slot 47 and leg 29. Once head 44 is positioned beneath slot 47, it cannot move upwardly through slot 47 because head 44 is too large to fit through slot 47. As a result, ends 35 and 37 are effectively locked together and, even if there is some lateral movement of legs 28 and 29, ends 35 and 37 moves simultaneously so that legs 28 and 29 continue to be in registration.

Yet another mechanism for maintaining legs 28 and 29 in registration is illustrated in FIG. 23. In FIG. 23, at least the distal end of at least one of legs 28 and 29 has magnetic properties, and a magnet 48 is used to interconnect legs 28 and 29. The magnet can be fixedly attached to leg 28 only, be fixedly attached to leg 29 only, or not be fixedly attached to either leg 28 and 29. As would be appreciated by those of skill in the art, if the magnet is not fixedly attached to either leg 28 and 29, then the distal end of each leg 28 and 29 must have magnetic properties.

In FIG. 22, a leg 28A is attached to a handle 56C at pivot point 49 such that leg 28A can pivot towards and away from leg 29. Legs 28A can be pivoted to a position in which leg 28 is parallel to leg 29. The structure of leg 28A is comparable to that of leg 28. Leg 28A has an elongate slot 38 formed therethrough.

As earlier described herein, foot 85 is shaped and dimensioned to slide along and through a sleeve 111. In order to facilitate the movement of a foot 85 through sleeve 111, one or more rolling balls 96 (FIG. 21) can be mounted on the bottom of foot 85. Ball 96 rolls over the bottom of sleeve 111 in the manner indicated by arrow R when foot 85 is displaced in the direction of arrow Q.

Having set forth our invention in terms to enable those skilled in the art to understand and practice the invention and having set forth the presently preferred embodiments and uses thereof.

The invention claimed is:
1. A method of installing a fiberglass cast on and cutting the cast for removal from an individual, comprising the steps of:
(a) providing a length of a pliable hollow thin-walled guide tube (110) with
(i) a top,
(ii) a bottom,
(iii) a length, and
(iv) open first and second ends;
(b) providing an elongate support tool (55) shaped and dimensioned to slide into and extend along said tube (110);
(c) providing a tool including
(i) a manually displaceable housing (77),
(ii) a motive power unit,
(iii) a cutting tool mounted in said housing and operated with said motive power unit;

(d) providing a guide (69) including
- (i) an upper leg (28) with a first distal end and a guide slot (38) formed therealong, and
- (ii) a lower leg (29) spaced apart from said upper leg (29), having a second distal end, and shaped and dimensioned to fit in and slide along said pliable guide tube, at least one of said upper leg and said lower leg displaceable between two operative positions,
- a first operative position in which said first and second distal ends are separable from one another, and
- a second operative position in which said first and second distal ends are engaged to maintain in registration said upper leg and said lower leg;

(e) sliding said support tool in said pliable guide tube;

(f) placing said guide tube and said support tool therein on an individual;

(g) applying at least first layer of fiberglass over a portion of said guide tube;

(h) applying at least a second layer of fiberglass over said first layer of fiberglass;

(i) sliding said support tool out of said guide tube;

(j) allowing said first and second layers of fiberglass to harden; and (k) at a subsequent time,
- (i) inserting said lower leg of said guide (69) in said tube (110) with said upper leg of said guide extending over said cast,
- (ii) engaging said first and second distal ends, and
- (iii) manually pushing said housing along said upper leg of said guide such that said cutting tool extends through and tracks along said guide slot (38) and cuts through said first and second layers of fiberglass.

\* \* \* \* \*